(12) United States Patent
Glowczwski

(10) Patent No.: US 10,939,517 B2
(45) Date of Patent: Mar. 2, 2021

(54) FEEDBACK CONTROL OF LIGHT EMITTING DEVICES USING FLUORESCENT COMPONENTS AND LIGHT SENSORS

(71) Applicant: SABER Corporation, Bryan, TX (US)

(72) Inventor: Alan Glowczwski, College Station, TX (US)

(73) Assignee: SABER CORPORATION, Bryan, TX (US)

( * ) Notice: Subject to any disclaimer, the term of this patent is extended or adjusted under 35 U.S.C. 154(b) by 0 days.

(21) Appl. No.: 16/875,861

(22) Filed: May 15, 2020

(65) Prior Publication Data

US 2020/0367334 A1     Nov. 19, 2020

Related U.S. Application Data

(60) Provisional application No. 62/848,526, filed on May 15, 2019.

(51) Int. Cl.
| | | |
|---|---|---|
| *A61L 2/10* | (2006.01) | |
| *H05B 45/12* | (2020.01) | |
| *A61L 2/00* | (2006.01) | |
| *A61L 15/42* | (2006.01) | |
| *H05B 45/325* | (2020.01) | |

(52) U.S. Cl.
CPC ............ *H05B 45/12* (2020.01); *A61L 2/0052* (2013.01); *A61L 15/42* (2013.01); *H05B 45/325* (2020.01); *A61L 2202/11* (2013.01); *A61L 2300/404* (2013.01)

(58) Field of Classification Search
CPC ............ H05B 37/0227; H05B 37/0245; H05B 37/0272; C02F 1/30; C02F 1/32; C02F 1/325; A23L 3/26; A23L 3/28; A61L 2/10; A61L 2/24

USPC ........................................... 315/307; 250/372
See application file for complete search history.

(56) References Cited

U.S. PATENT DOCUMENTS

| | | |
|---|---|---|
| 5,445,608 A | 8/1995 | Chen et al. |
| 5,616,140 A | 4/1997 | Prescott |
| 5,944,748 A | 8/1999 | Mager et al. |
| 6,267,779 B1 | 7/2001 | Gerdes |
| 6,290,713 B1 | 9/2001 | Russell |
| 6,443,978 B1 | 9/2002 | Zharov |
| 6,730,113 B2 | 5/2004 | Eckhardt et al. |

(Continued)

FOREIGN PATENT DOCUMENTS

EP           3275506 A1     1/2018

OTHER PUBLICATIONS

João Cabral et al. "Blue Light Disinfection in Hospital Infection Control: Advantages, Drawbacks, and Pitfalls", Antibiotics, 2019, 21 pages, vol. 8, No. 58.

*Primary Examiner* — Tung X Le
(74) *Attorney, Agent, or Firm* — Talem IP Law, LLP

(57) ABSTRACT

A method of controlling application of a dose of light energy for treatment to disinfect an area includes causing the dose of light energy to be emitted from at least one light emitting device, receiving a wavelength and intensity of light emitted from a fluorescent component within the area being disinfected by the dose of light energy, and adjusting at least one of a current, a voltage, a pulse width, and a pulse frequency applied to the at least one light emitting device based on the received wavelength and intensity of the light emitted from the fluorescent component.

20 Claims, 8 Drawing Sheets

(56) References Cited

U.S. PATENT DOCUMENTS

| | | |
|---|---|---|
| 8,372,128 B2 | 2/2013 | Reuben |
| 10,022,555 B2 | 7/2018 | Tapper et al. |
| 2001/0047144 A1 | 11/2001 | Tillotson et al. |
| 2003/0009158 A1 | 1/2003 | Perricone |
| 2003/0114902 A1 | 6/2003 | Prescott |
| 2004/0008523 A1 | 1/2004 | Butler |
| 2005/0288746 A1 | 12/2005 | Perez |
| 2006/0167532 A1 | 7/2006 | Parker |
| 2006/0206173 A1 | 9/2006 | Gertner et al. |
| 2007/0233208 A1 | 10/2007 | Kurtz et al. |
| 2008/0058689 A1 | 3/2008 | Holloway et al. |
| 2008/0269849 A1 | 10/2008 | Lewis |
| 2009/0143842 A1 | 6/2009 | Cumbie et al. |
| 2009/0198173 A1 | 8/2009 | Samuel et al. |
| 2012/0126134 A1* | 5/2012 | Deal ................. A61L 2/24 250/372 |
| 2015/0148734 A1 | 5/2015 | Fewkes et al. |
| 2015/0238774 A1 | 8/2015 | Anderson et al. |
| 2017/0100495 A1* | 4/2017 | Shur .................. H04N 5/332 |
| 2017/0245527 A1* | 8/2017 | Dobrinsky ............. A23B 9/06 |
| 2017/0290934 A1* | 10/2017 | Dobrinsky ......... G02B 19/0095 |
| 2018/0043043 A1 | 2/2018 | Spector |
| 2018/0056087 A1 | 3/2018 | Ribeiro et al. |
| 2018/0117189 A1* | 5/2018 | Yadav ................ A61N 5/0613 |
| 2018/0221521 A1* | 8/2018 | Shur .................... A61L 2/00 |

* cited by examiner

FEEDBACK CONTROL OF LIGHT EMITTING DEVICES USING FLUORESCENT COMPONENTS AND LIGHT SENSORS

BACKGROUND

Healthcare associated infections are a major problem in the healthcare industry. In addition, bacterial infections are the most common healthcare associated infections. Bacteria can increase recovery time for not only surgical patients but also any patient who has non-intact skin, such as wounds, burns, and ulcers. When a surgical patient contracts a healthcare associated infection at a hospital, the patient usually requires a longer stay in the hospital because the recovery time is increased, resulting in a large increase in the cost to the hospital and the patient. Some patients, such as the elderly and small children, are more prone to the risk of infection.

Furthermore, certain bacteria and viruses, such as SARs-Cov-2 virus responsible for Covid-19 and influenzas, are easily spread from person to person and by contact with many different types of surfaces. Spread of bacteria and viruses cause undo burden on patients and healthcare systems and can be spread to anyone without immunity (e.g., via a vaccination). Therefore, it is important to prevent bacterial and viral infections by providing effective treatment to potentially compromised surfaces on a patient and both in and out of hospitals.

BRIEF SUMMARY

Methods and systems that can maintain proper light dose of energy are provided. Non-intact skin (e.g., a wound), as well as other surfaces that may harbor bacteria and/or viruses, (hereinafter "potentially compromised surfaces") can be treated with a sufficient dose of light energy (e.g., from a light emitting device ("LED")) in order to kill the bacteria/virus. Feedback sensors, which capture light emitted from fluorescent material in and around the potentially compromised surfaces, are used to measure the dose of light energy to ensure that the sufficient dose of light energy is provided to all areas of the potentially compromised surfaces.

A method of controlling application of a dose of light energy for treatment to disinfect an area (of a potentially compromised surface) includes causing the dose of light energy to be emitted from one or more light emitting devices, receiving a wavelength and intensity of light emitted from a fluorescent component within the area being disinfected by the dose of light energy, and adjusting at least one of a current, a voltage, a pulse width (e.g., for pulse width modulation), and a pulse frequency (e.g., for frequency modulation) applied to the one or more light emitting devices based on the received wavelength and intensity of the light emitted from the fluorescent component.

In some cases, the method further includes determining that the wavelength and intensity of light emitted from the fluorescent component within the area being disinfected by the dose of light energy has been applied for a predetermined length of time, and upon determining that the wavelength and intensity of light emitted from the fluorescent component within the area being disinfected by the dose of light energy has been applied for the predetermined length of time, causing the dose of light energy being emitted from the one or more light emitting devices to cease. The light wavelength emitted from the fluorescent component will be different from the emitted light wavelength from the source. This wavelength of fluorescent light and intensity of light can be measured by sensors. In some cases, the method further includes upon determining the wavelength and intensity of light emitted from the fluorescent component within the area being disinfected by the dose of light energy has been applied for the predetermined length of time, sending a notification that the area being disinfected by the dose of light energy has been successfully disinfected.

In some cases, the fluorescent component within the area being disinfected by the dose of light energy is made of fluorescent thread. In some cases, the fluorescent component is arranged within the area being disinfected as a fluorescent grid. In some cases in which the fluorescent component is arranged in the fluorescent grid, the dose applied to each portion of the grid can be independently controlled based on the emission from the fluorescent component of that portion of the grid.

A system for controlling application of a dose of light energy for treatment to disinfect an area includes one or more light emitting devices, a fluorescent component within the area being disinfected by the dose of light energy, one or more sensors capable of receiving a wavelength and intensity of light emitted from the fluorescent component within the area being disinfected by the dose of light energy, and a controller coupled to the one or more sensors, the controller being configured to: cause the dose of light energy to be emitted from the one or more light emitting devices, receive, via the one or more sensors, a wavelength and intensity of light emitted from the fluorescent component within the area being disinfected by the dose of light energy, and adjust at least one of a current, a voltage, a pulse width (e.g., for pulse width modulation), and a pulse frequency (e.g., for frequency modulation) applied to the one or more light emitting devices based on the received wavelength and intensity of the light emitted from the fluorescent component. In some cases, the system includes at least two light emitting devices where each light emitting device can be independently controlled by the controller.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Methods and systems that can maintain proper light dose of energy are provided. Non-intact skin (e.g., a wound), as well as other surfaces that may harbor bacteria and/or viruses, ("potentially compromised surfaces") can be treated with a sufficient dose of light energy (e.g., from a light emitting device (LED)) in order to kill the bacteria/virus. Feedback sensors, which capture light emitted from fluorescent material in and around the potentially compromised surfaces, are used to measure the dose of light energy applied to the potentially compromised surfaces to ensure that the sufficient dose of light energy is provided to all areas of the potentially compromised surfaces. Advantageously, the fluorescent emission can enable a more accurate determination of dose than simply sensing the reflection of the light emitted from the LED(s).

Figure 1:
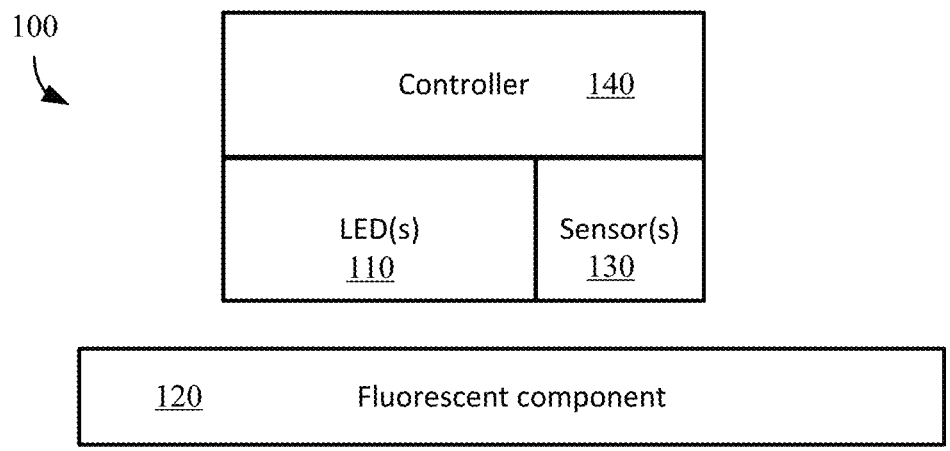
FIG. 1 illustrates a representational diagram of a light disinfection system for delivering light treatment to a potentially compromised surface based on fluorescent feedback.

FIG. 1 illustrates a representational diagram of a light disinfection system for delivering light treatment to a potentially compromised surface based on fluorescent feedback. Referring to FIG. 1, a light disinfection system 100 for controlling application of a dose of light energy for treatment to disinfect an area includes at least one LED 110, a fluorescent component 120 within the area being disinfected by the dose of light energy, at least one sensor 130 capable of sensing a wavelength and corresponding intensity of light emitted from the fluorescent component 120 within the area being disinfected by the dose of light energy, and a controller 140 coupled to the at least one sensor 130 and the at least one LED 110. Connections and communication between the controller 140, the LED(s) 110, and the at least one sensor 130 may be wired or wireless. The LED(s), sensor(s), controller, and fluorescent component may be packaged in a variety of configurations. In some cases, a substrate holding the LEDs 110 and fluorescent light sensors 130 can be a flexible substrate such as for a bandage. In some cases, a substrate holding the LEDs 110 and the fluorescent light sensors 130 can be molded to a shape of the surface receiving the dose of light energy.

The controller 140 can be hardware (e.g., logic gates; digital and/or analog circuitry) or a combination of hardware (e.g., processor) and software (where the software is stored in a storage medium) It should be understood that as used herein, in no case do the terms "storage medium," "computer-readable storage media" or "computer-readable storage medium" consist of transitory carrier waves or propagating signals.

The at least one sensor 130 can include a light sensor that detects the light emitted from the fluorescent component 120. The controller 140 can receive a signal from the light sensor and control an output of the at least one LED 110 based on the signal received from the light sensor. For example, the controller 140 can receive a signal from the light sensor that includes or indicates the intensity of the detected light of corresponding wavelength. The controller can adjust the output of the LED(s) 110 based on the signal received from the light sensor to ensure that the proper dose of light energy is being applied to a potentially compromised surface.

Figure 2A:
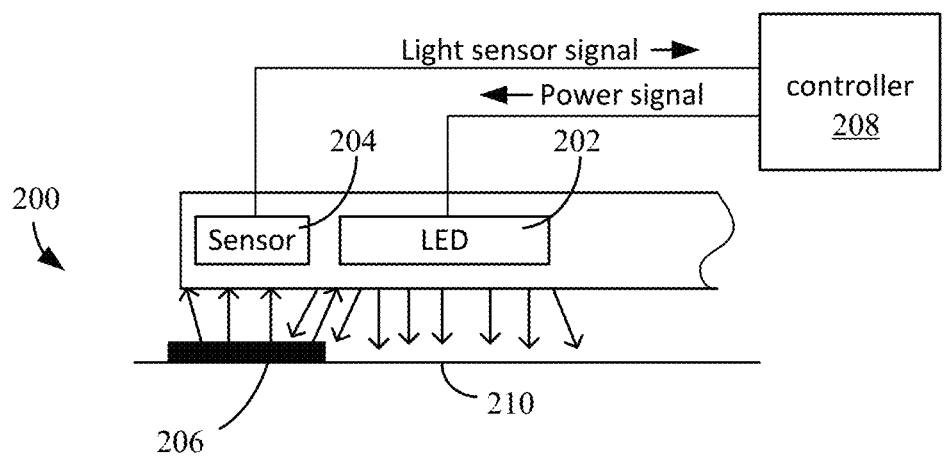
FIG. 2A is an example representation of a light disinfection system with fluorescent feedback.
Figure 2B:
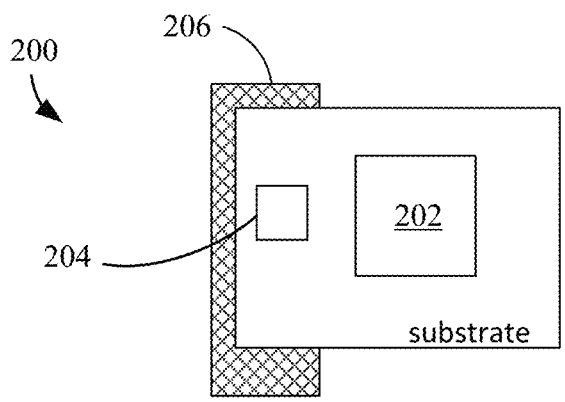
FIG. 2B is a top view representation of the LED portion of the light disinfection system of FIG. 2A.

FIG. 2A is an example representation of a light disinfection system with fluorescent feedback; and FIG. 2B is a top view representation of the LED portion of the light disinfection system of FIG. 2A. As described with respect to FIG. 1, in the configuration 200 illustrated in FIGS. 2A and 2B, a light disinfection system 200 includes at least one LED 202, at least one sensor 204, at least one fluorescent component 206, and a controller 208.

In operation, the controller 208 receives a signal from the sensor 204 and can adjust at least one of a current, a voltage, a pulse width (e.g., for pulse width modulation), and a pulse frequency (e.g., for frequency modulation) applied to the LED 202. The power applied to the LED 202 affects the intensity of the emission from the LED 202. Thus, the adjustment of the power to the LED 202 can be used to adjust the intensity of the LED 202. The LED 202 emits light to a surface 210 at an intensity and length of time according to a specified dose protocol. The light emitted from the LED 202 can be a specific wavelength (e.g., about 405 nanometers) that is used to provide disinfecting properties.

The light emitted from the LED 202 excites the atoms in the fluorescent component 206, causing the fluorescent component 206 to emit light at a different wavelength (e.g., about 570 nanometers). That is, the fluorescent component 206 absorbs the light (electromagnetic radiation) that impinges its surface from the LED 202 and re-emits light at a fluorescent wavelength. The re-emitted light from the fluorescent component 206 is detected by the sensor 204. Sensor 204 can be a fluorescent light sensor that detects light emitted at the wavelength emitted by the fluorescent component 206 (e.g., 570 nanometers). A relationship between the measured wavelengths and intensity of the light from the fluorescent component 206 and the intensity of the primary light output from the LED 202 can be used by the controller 208 to determine whether the appropriate dose is being provided by the LED 202.

Advantageously, by using the emission of a fluorescent component instead of just reflectance of the LED from the surface being disinfected, it is possible to more accurately determine dose of light energy from the LED. In addition, the wavelengths emitted from the fluorescent material are easier to detect than the wavelengths of light from the LED themselves and in some cases it is possible to avoid interference noise caused from light that is not intended to be detected (e.g., normal room lighting) and that does not kill the bacteria/virus. This unintended detection may lead to an insufficient dose of light energy being applied to a potentially compromised surface due to feedback sensors detecting more light than is actually being emitted by the other disinfection systems.

Figure 3A:
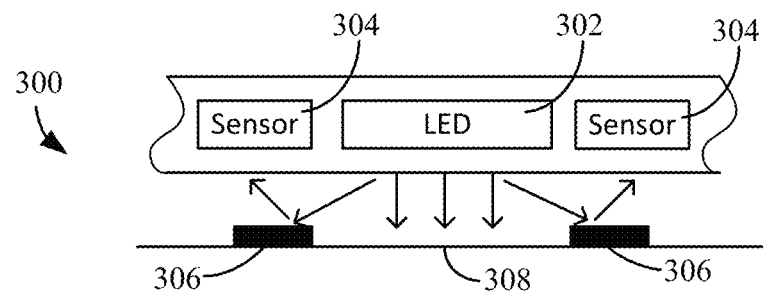
FIGS. 3A-3C illustrate example configurations of the LED, sensor, and fluorescent components of a light disinfection system.
Figure 3B:
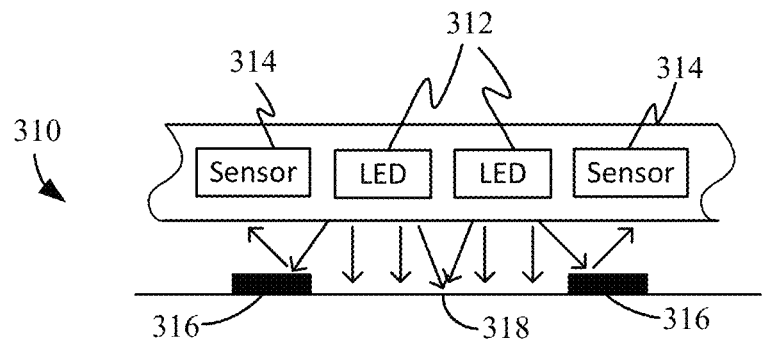
Figure 3C:
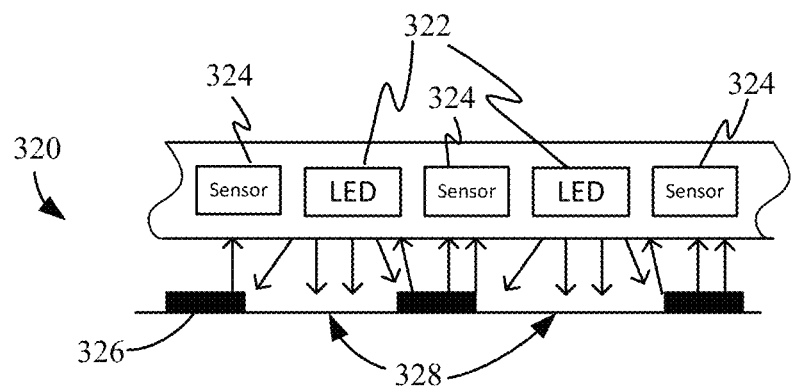

FIGS. 3A-3C illustrate example configurations of the LED, sensor, and fluorescent components of a light disinfection system. In the example shown in FIG. 3A, a light disinfection system 300 includes one LED 302 and at least two light sensors 304 at sides of the LED 302. Of course, some implementations may use a single light sensor at one side of one or more LEDs. A fluorescent component 306 is disposed around an area 308 to be disinfected. The fluorescent component 316 may have a rectangular shape or other polygon with a central opening or may be formed of one or more strips that can be disposed at an outer part of the area 308 (e.g., on one or more sides).

In the example shown in FIG. 3B, a light disinfection system 310 includes a plurality of LEDs 312 instead of the single LED 302. Here, at least two light sensors 314 are disposed at an outer boundary of the plurality of LEDs 312. Similar to the example shown in FIG. 3A, a fluorescent component 316 is disposed around an area 318 to be disinfected. The fluorescent component 316 may have a rectangular shape or other polygon with a central opening or may be formed of one or more strips that can be disposed at an outer part of the area 318 (e.g., on one or more sides).

In the example shown in FIG. 3C, a light disinfection system 320 includes a plurality of LEDs 322 similar to the example of FIG. 3B; however, instead of the at least two light sensors being disposed at only an outer boundary, light sensors 324 are interspersed between the LEDs of the plurality of LEDs 322. Similarly, fluorescent component 326 can be arranged within area 328 that is being disinfected. In some cases, fluorescent component 326 can be arranged in a grid pattern.

In some cases, the fluorescent component 306, 316, 326 is disposed on a same substrate as at least the LED(s) 302, 312, 322 and sensors 304, 314, 324, but on an opposite side. In such a case, the at least one LED 302, 312, 322 is positioned to emit light through the substrate. In some cases, the fluorescent component 306, 316, 326 may be included separately from the light disinfection system 300, 310, 320 and can be separately attached or arranged around (and in some cases within) the area being disinfected.

Figure 4A:
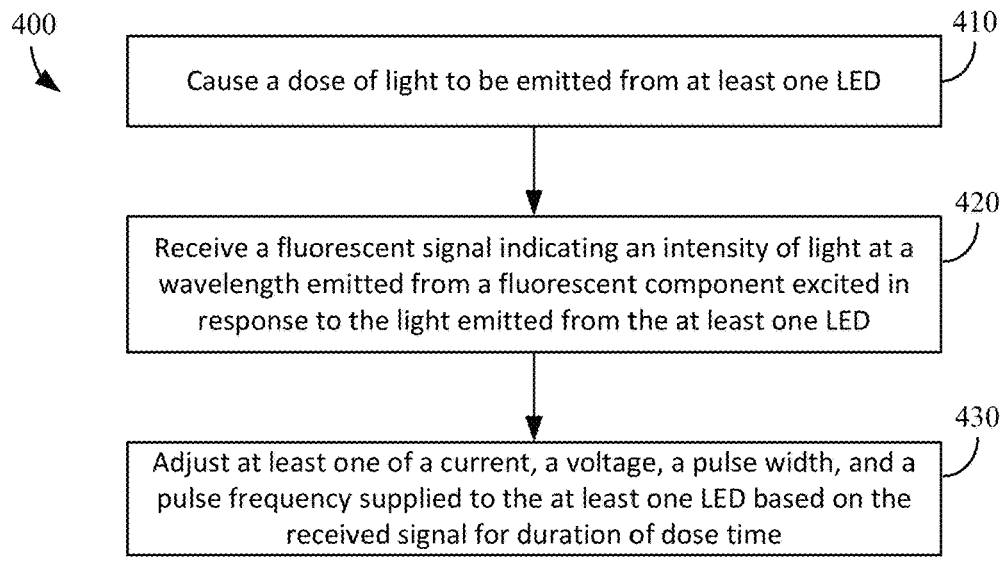
FIG. 4A illustrates an example method of treating a potentially compromised surface with a dose of light energy.

FIG. 4A illustrates an example method of treating a potentially compromised surface with a dose of light energy. The method 400 (executed by the controller) may begin, for example, by causing (410) a dose of light energy to be emitted from one or more light emitting devices. The dose of light energy is at a wavelength (e.g., measured in nanometers) and intensity (e.g., measured in milliwatts per cm2 or lumens or lux) of light to kill viruses and/or bacteria. The controller can cause a dose of light energy to be emitted from the one or more light emitting devices by sending a signal applying power to the at least one LED, causing the LED(s) to illuminate (e.g., turns the at least one LED on).

When the light (i.e., photons) emitted from the one or more light emitting devices (e.g., LEDs) reaches the fluorescent component, the atoms within the fluorescent component become excited; as the atoms return to normal, the energy that excited the atoms is released as photons (i.e., light). Therefore, the fluorescent component "emits" light itself (as opposed to simply reflecting the light that is emitted from the one or more light emitting devices). As previously explained, the light emitted from the fluorescent component is a different wavelength and intensity of light than the light emitted from the one or more light emitting devices.

The method 400 continues by receiving (420) a fluorescent signal indicating an intensity of light at a wavelength emitted from the fluorescent component excited in response to the light emitted by the at least one LED while the area is being disinfected by the dose of light energy. In some cases, the signal is received from a light sensor.

Figure 4B:
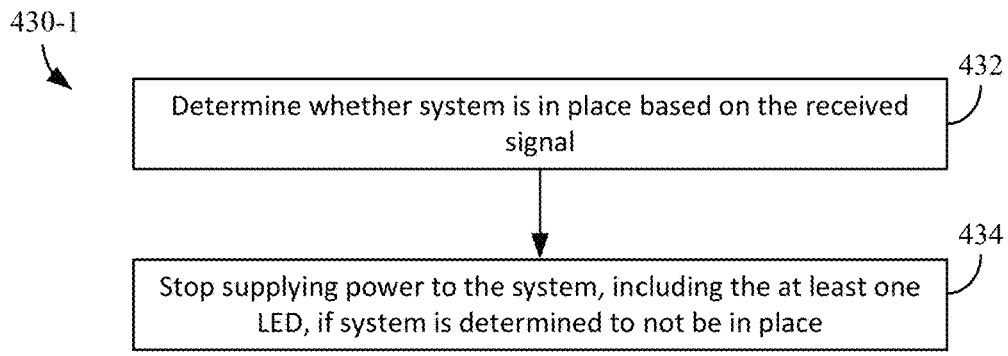
FIGS. 4B and 4C illustrate example adjustment methods.

The method 400 further includes adjusting (410) at least one of a current, a voltage, a pulse width, and a pulse frequency applied to the at least one LED based on the received signal for a duration of dose time. In some cases, the controller can control the current and/or voltage by adjusting resistance (e.g., for a voltage divider when adjusting voltage or on the line when adjusting current). In some cases, the controller can perform pulse width modulation and/or frequency modulation by adjusting duty cycle and/or frequency Referring to FIG. 4B, in some cases, the adjusting step can include process 430-1, which involves determining (432) whether the system is in place based on the received fluorescent signal; and stopping (434) the supply of power to the LEDs if the system is determined to not be in place (e.g., causing the dose of light energy being emitted from the LEDs to cease). Process 430-1 thus can be used to prevent operation of the system unless the LEDs are in place.

Figure 4C:
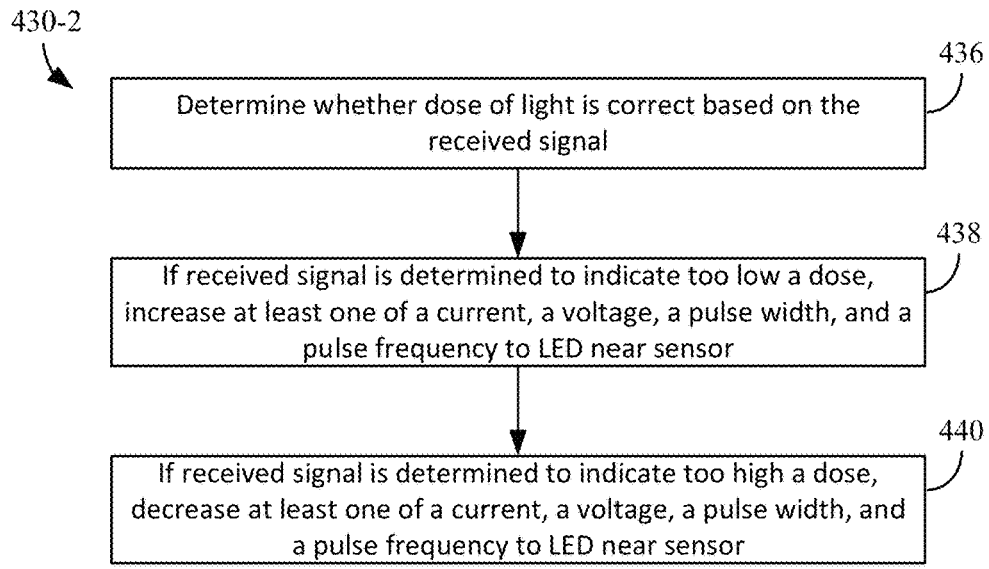

Referring to FIG. 4C, in some cases, the adjusting step can include process 430-2, which involves determining (436) whether the dose of light energy is correct based on the received signal; if the received signal is determined to indicate too low a dose, increasing (438) at least one of a current, a voltage, a pulse width and a pulse frequency applied to an LED near the sensor providing the signal; and if the received signal is determined to indicate too high a dose, decreasing (440) at least one of the current, the voltage, the pulse width and the pulse frequency supplied to the LED near the sensor providing the signal.

A controller can have access to pre-stored information about how different wavelengths and intensities of light produced by the fluorescent component correspond to the light (e.g., lux) being emitted by an LED of the light disinfection system. This pre-stored information can be used by the controller to determine not only whether to adjust at least one of the current, the voltage, the pulse width and the pulse frequency applied to the one or more light emitting devices, but also in some cases, by what increment to perform the adjustment. Of course, In some cases, the controller performs an incremental adjustment until the fluorescent signal indicates the proper LED dose. In some cases, the controller can calculate (e.g., by executing an algorithm using received measurements of wavelength and intensity of light from the fluorescent component as inputs) the amount that at least one of the current, the voltage, the pulse width and the pulse frequency need to be changed (e.g., positive/increasing or negative/decreasing change) to deliver an optimal dose of light energy to the potentially compromised surface. In some cases, the controller can simply retrieve a value corresponding to the amount that at least one of the current, the voltage, the pulse width and the pulse frequency need to be changed to deliver an optimal dose of light energy to the potentially compromised surface by accessing the pre-stored information corresponding to the received measurements wavelength and intensity of light from the fluorescent component.

One or both of processes 430-1 and 430-2 may be performed as part of the adjusting step 430.

In some cases, a specific wavelength of light and/or a specific intensity of light emitted by the fluorescent component (and subsequently received by the light sensor(s)) may be considered optimal. In some cases, a specific range of wavelength of light and/or a specific intensity of light emitted by the fluorescent component (and subsequently received by the light sensor(s)) may be considered optimal. There may be other specific wavelengths (or ranges of wavelengths) and other specific intensities of light (or ranges of intensities of light) emitted by the fluorescent component (and subsequently received by the light sensor(s)) that may be considered sub-optimal. There may be other specific wavelengths (or ranges of wavelengths) and other specific intensities of light (or ranges of intensities of light) emitted by the fluorescent component (and subsequently received by the light sensor(s)) that may be considered not usable.

It should be understood that, due to the relationship between the wavelength and intensity of light emitted from the one or more light emitting devices and the wavelength and intensity of light emitted from the fluorescent component, the adjustment of at least one of the current, the voltage, the pulse width and the pulse frequency applied to the one or more light emitting devices can produce a corresponding change in the wavelength and intensity of light emitted from the fluorescent component.

As mentioned above, step 430 is performed during a duration of dose time. Accordingly, the controller can determine whether the appropriate dose was applied for the predefined period of time based on the sensor detecting the light emitted from the fluorescent component. For example, the controller can receive the signal corresponding to the intensity of light emitted from the fluorescent component continuously or at fixed intervals (or other pattern). In some cases, the controller can operate the light sensor(s) to enable the sensors to obtain the measurements continuously or at the fixed intervals (or other pattern) or even in response to a particular trigger. In some cases, the ability to adjust intensity of the LEDs involves applying a particular duty cycle to the power delivered to the LEDs. The sensors can be operated during the full period even though the LEDs may not be on during that full period.

The duration of dose time can be a predetermined length of time that a particular amount of light energy (e.g., lux) is applied to a surface. The predetermined period of time may be predetermined based on a type of the potentially compromised surface (e.g., the type and/or severity of the patient's wound or type of inanimate surface). The controller can ensure that the proper dose has been applied not just by ensuring LEDs are emitting the correct intensity, but also that the correct intensity was emitted for the proper dose time, such as illustrated in the examples shown in FIGS. 5A and 5B.

Furthermore, in some cases, the controller can, while process 400 is being carried out, determine whether the length of time the LED(s) have been operated are considered optimal, sub-optimal, and not usable, and then adding those times together to determine whether the pre-determined length of time has been reached. In regards to the determination of whether the pre-determined length of time has been reached, the length of time that the controller receives a fluorescent signal that is considered optimal may be weighted differently than the length of time the controller receives a fluorescent signal that is considered sub-optimal. The length of time that the controller receives a fluorescent signal that is considered not usable may not be given any weight towards the determination of whether the pre-determined length of time has been reached.

As an example, a predetermined length of time for a dose of light energy could be 60 minutes. If the controller receives 30 minutes of measurements of wavelengths and intensities of light from the fluorescent component that are considered optimal, 30 minutes of measurements of wavelengths and intensities of light from the fluorescent component that are considered sub-optimal, and 10 minutes of measurements of wavelengths and intensities of light from the fluorescent component that are considered not usable, the predetermined length of time may not be reached. The predetermined length of time may not be reached because the 30 minutes of measurements of wavelengths and intensities of light from the fluorescent component that are considered sub-optimal may only be given a weight of 0.75 (e.g., resulting in 30 minutes*0.75=22.5 minutes) and the 10 minutes of measurements of wavelengths and intensities of light from the fluorescent component that are considered not usable being given a weight of zero (e.g., resulting in 10 minutes*0=0 minutes), which falls short of the 60 minutes for the predetermined length of time for a dose of light energy (e.g., 30 minutes+22.5 minutes+0 minutes=52.5 minutes), even though the actual time the dose of light energy was emitted from the one or more emitting devices was over 60 minutes (e.g., 30 minutes+30 minutes+10 minutes=70 minutes). Continuing with the example above, if the controller then receives 7.5 additional minutes of measurements of wavelengths and intensities of light from the fluorescent component that are considered optimal, the predetermined length of time for a dose of light energy will be reached.

In some cases, after a certain length of time receiving measurements of wavelengths and intensities of light from the fluorescent component that are considered not usable, the predetermined length of time for a dose of light energy will need to be restarted. As an example, if the controller first received 30 minutes of measurements of wavelengths and intensities of light from the fluorescent component that are considered optimal, then received 30 minutes of measurements of wavelengths and intensities of light from the fluorescent component that are considered not usable, the predetermined length of time for a dose of light energy may need to be restarted (e.g., meaning that the 30 minutes of optimal time are no longer counted towards the predetermined length of time for a dose of light energy).

In some cases, if the actual length of time for a dose of light energy exceeds a maximum length of time, the predetermined length of time for the dose of light energy will need to be restarted. However, the maximum length of time for a dose of light energy can be performed on a rolling basis. As an example, a maximum length of time for a dose of light energy may be 90 minutes and a predetermined length of time for a dose of light energy is 60 minutes. If the controller first received 30 minutes of measurements of wavelengths and intensities of light from the fluorescent component that are considered sub-optimal (e.g., with a weight of 0.5), then received 20 minutes of measurements of wavelengths and intensities of light from the fluorescent component that are considered not usable, then received 40 minutes of measurements of wavelengths and intensities of light from the fluorescent component that are considered sub-optimal (e.g., with a given weight of 0.75), the predetermined length of time for a dose of light energy will need to be restarted because the maximum length of time for a dose of light energy has been reached (e.g., 30 minutes+20 minutes+40 minutes=90 minutes), yet the predetermined length of time for a dose of light energy has not been reached (e.g., (30 minutes*0.5)+(20 minutes*0)+(40 minutes*0.75)=45 minutes). However, in some cases in which the maximum length of time for a dose of light energy is done on a rolling basis, if the controller then receives 30 minutes of measurements of wavelengths and intensities of light from the fluorescent component that are considered optimal, the predetermined length of time for a dose of light energy is reached (e.g., (40 minutes*0.75)+30 minutes=60 minutes) and the maximum length of time for a dose of light energy has not been reached (e.g., 40 minutes+30 minutes=70 minutes<90 minutes).

In some cases, upon determining that the predetermined length of time for a dose has been completed, the system can turn off. In some cases, a notification (e.g., to a user computing device or to an external indicator) can be sent that the area being disinfected by the dose of light energy has been successfully disinfected.

Figure 5A:
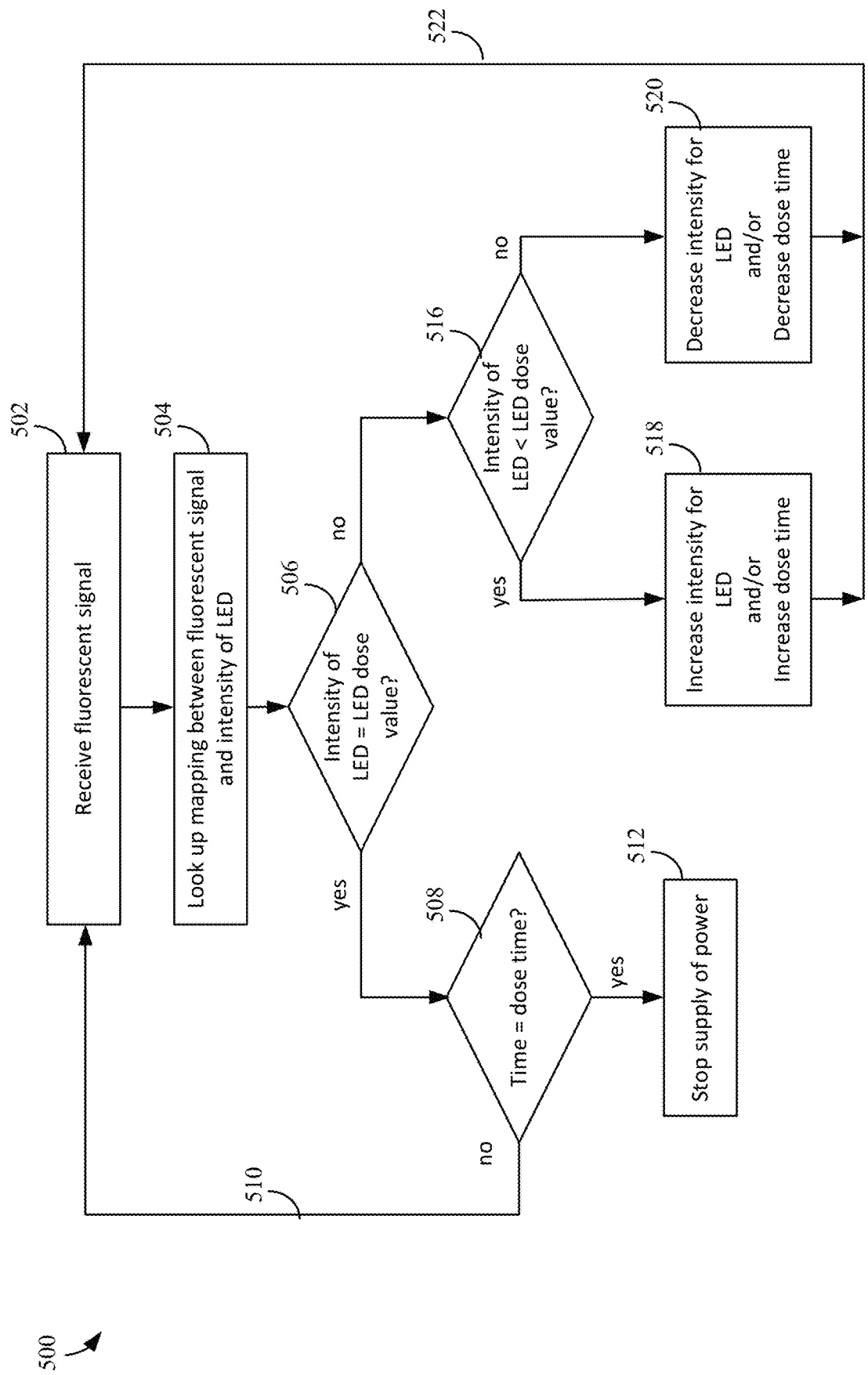
FIGS. 5A and 5B illustrate specific implementations for adjusting an LED of a light disinfection system.
Figure 5B:
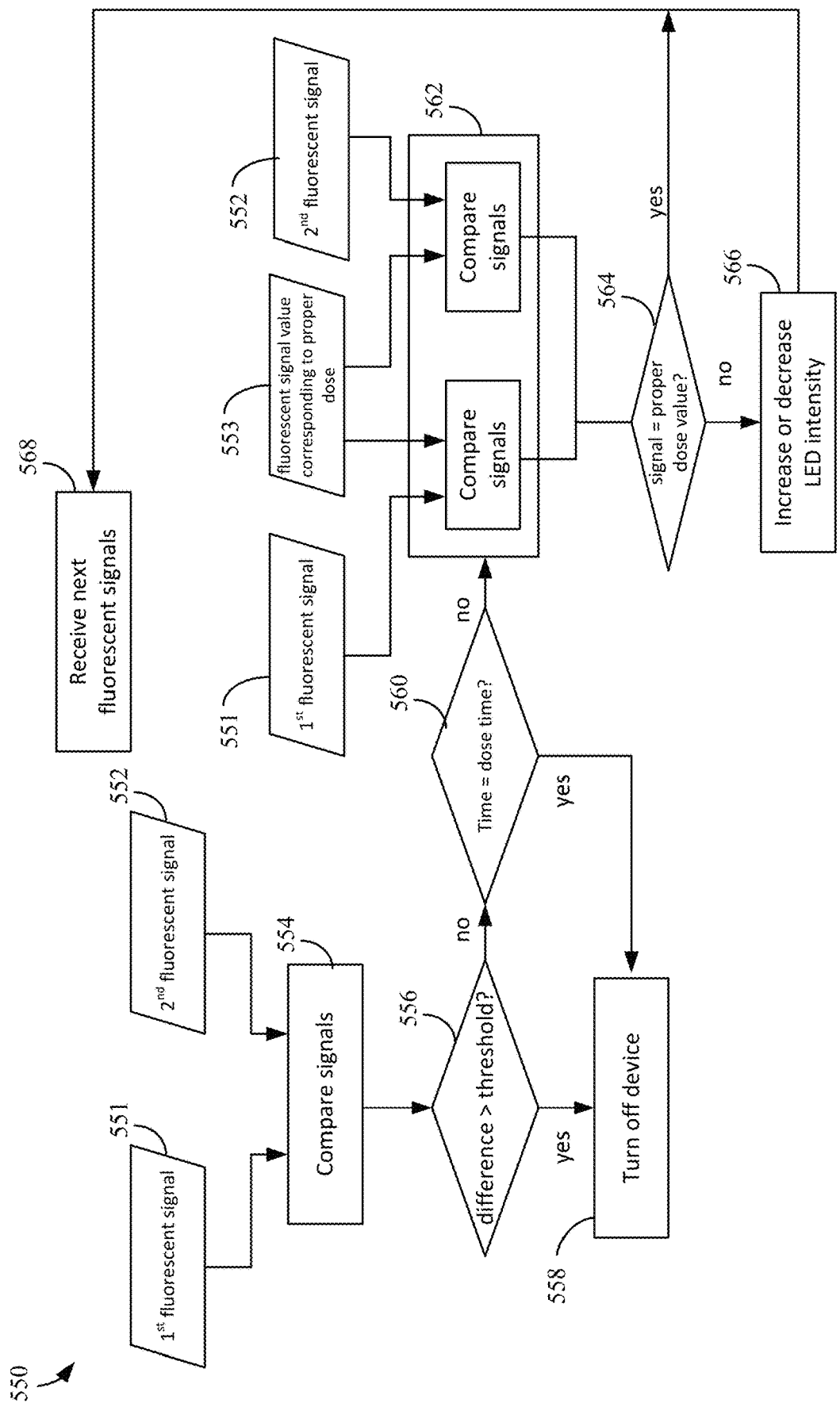

FIGS. 5A and 5B illustrate specific implementations for adjusting an LED of a light disinfection system. As previously mentioned, the light intensity from the at least one LED can be adjusted based on a received fluorescent signal in order to provide a desired dose of light energy to an area.

In addition to the intensity of the at least on LED, the dose involves application of that intensity for a predetermined amount of time.

Referring to FIG. 5A, a method 500 can include receiving a fluorescent signal (502) and looking up a mapping between the fluorescent signal and the intensity of the LED (504), A determination (506) can be made regarding whether the intensity identified by the mapping is equal to (or within range of) the LED dose value. If the determination 506 indicates that the intensity identified by the mapping is the LED dose value, a determination 508 can be made regarding whether the predetermined time for the dose time has passed. If the determination 508 indicates that the time has not yet passed, then the process repeats (510). If the determination 508 indicates that the time has satisfied the dose time, the controller stops the supply of power to the system (512) since the disinfection should be complete.

If the determination 506 indicates that the intensity identified by the mapping is not the LED dose value, a determination 516 can be made regarding whether the intensity identified by the mapping is less than the LED dose value. If the determination 516 indicates that the intensity identified by the mapping is less than the LED dose value, the controller can increase the intensity for the LED (518). This may be accomplished by increasing the current and/or voltage or by adjusting the duty cycle and/or pulse width turning on the LEDs. In some cases, instead of or in addition to adjusting the power to the LEDs, the dose time may be increased. If the determination 516 indicates that the intensity identified by the mapping is greater than the LED dose value, the controller can decrease the intensity for the LED (520). This may be accomplished by decreasing the current and/or voltage or by adjusting the duty cycle and/or pulse width turning on the LEDs. In some cases, instead of or in addition to adjusting the power to the LEDs, the dose time may be decreased. After adjusting the intensity of the LEDs (e.g., step 518 or 520), the process repeats (522).

Referring to FIG. 5B, in this implementation, one or more comparators can be coupled to the sensors to perform comparison operations. Some of such implementations may be carried out entirely by logic circuitry (and optional analog to digital conversion). In the illustrated example, a method 550 can include comparing (554) a first fluorescent signal 551 and a second fluorescent signal 552 from a corresponding two sensors. A determination (556) can then be made regarding whether there is a difference and if that difference is larger than a threshold value. If the difference is larger than a threshold value, the system can be turned off (558). This approach assumes that if one side has lifted up and away from the surface, but the other side is still in place, then it is likely that the system has been moved in a manner that could cause light from the LEDs to hit a person's eyes.

If the determination 556 indicates that there is no difference or the difference is less than a threshold value, a determination 560 can be made regarding whether the predetermined time for the dose time has passed. If the determination 560 indicates that the time has satisfied the dose time, the controller stops the supply of power to the system (512) since the disinfection should be complete. If the determination 560 indicates that the time has not yet passed, then the process continues with comparing (562) the signals 551, 552 to a fluorescent signal value corresponding to a proper dose. If the determination 560 indicates that the signal does not satisfy conditions of a proper dose value, then the system can adjust (566) the LED intensity (e.g., increase or decrease LED intensity as needed) and the process repeats with receiving the next fluorescent signals (568).

Figure 6A:
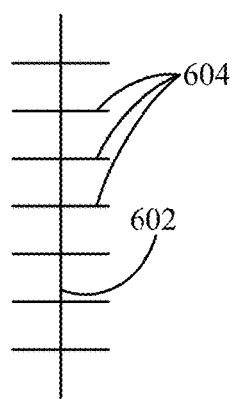
FIGS. 6A-6E illustrate an example application of a light disinfection system for delivering light treatment to a potentially compromised surface based on fluorescent feedback.

FIGS. 6A-6E illustrate an example application of a light disinfection system for delivering light treatment to a potentially compromised surface based on fluorescent feedback. FIG. 6A illustrates a state of a wound (e.g., incision) 602 of a patient that has been treated with a plurality of sutures 604. Of course, it should be understood that the described light disinfection system can be applied to wounds that have been treated with stitches and/or staples and/or adhesives and even wounds that have not been sealed or inanimate surfaces that need to be disinfected from viruses and/or bacteria (e.g., surfaces and/or surfaces of devices in hospitals).

Figure 6B:
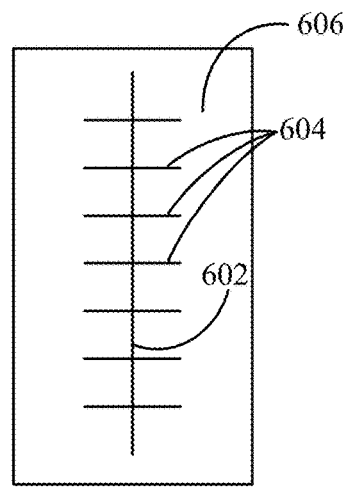
Figure 6C:
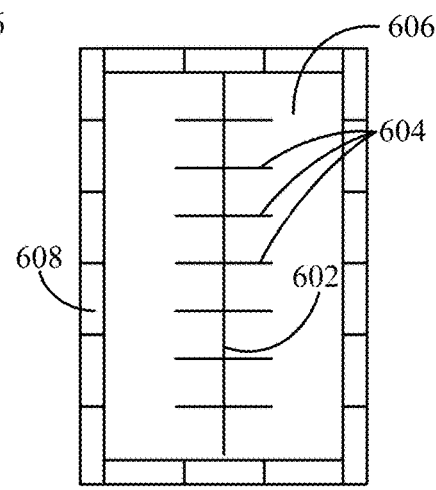
Figure 6D:
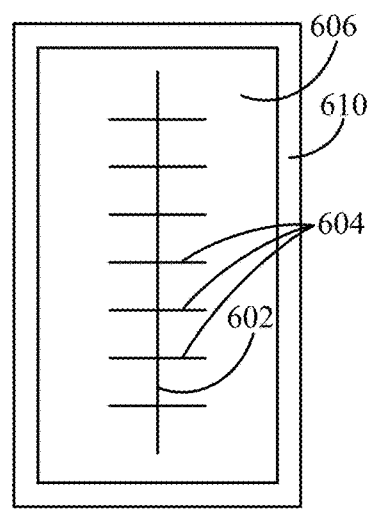

Referring to FIG. 6B, a clear adhesive bandage 606 may be applied over the wound 602 of the patient. In some cases, such as when an inanimate surface is to be disinfected, the clear adhesive bandage would be omitted. Then, as illustrated in FIG. 6C, a fluorescent component 608 is applied to outer edges of the clear adhesive bandage 606. The fluorescent component 608 may be available with the supplies such as the clear adhesive bandages 606 or provided in a kit with a light disinfection system. Alternatively, as illustrated in FIG. 6D, the fluorescent component 610 may be integrated within portions of the clear adhesive bandage 606 (e.g., during manufacture). That is, the fluorescent component 608 can be disposed on or in a transparent bandage. In some cases, the fluorescent component 608 or 610 is able to attach to the potentially compromised surface (e.g., via an adhesive). In the case of a wound, a fluorescent component may be integrated within the wound as suture thread used in the plurality of sutures 604. In the case of an inanimate object, a fluorescent component may be integrated within the surface of the inanimate object (e.g., as a fluorescent thread). In some cases, a grid of fluorescent material can be arranged.

Figure 6E:
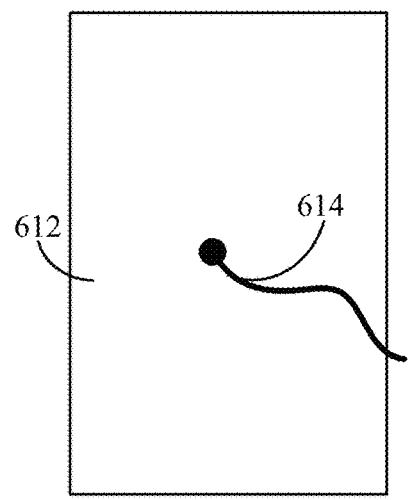

As illustrated in FIG. 6E, a light emitting device 612 can be placed over the wound 602 to begin disinfection (e.g., method 400). The light emitting device 612 can be disposed on the transparent bandage and above the fluorescent component 608. The light emitting device 612 may be directly above or simply in a vertical plane above (e.g., overlapping or not overlapping) the fluorescent component 608. Similarly, the light sensor (not shown) may be directly above or simply in a vertical plane above (e.g., overlapping or not overlapping) the fluorescent component 608. In some cases, the light emitting device 612 is securely attached to the clear adhesive bandage 606 (e.g., via a double-sided adhesive). In some cases, the light emitting device 612 includes a cord 614 for attachment to an external power source. In some cases, the light emitting device 612 is battery powered and therefore does not include a cord 614 for attachment to an external power source. In some cases, the light emitting device 612 is battery powered and includes a cord 614 for attachment to an external power source.

In some cases, the fluorescent component within the area being disinfected by the dose of light energy is arranged in a fluorescent grid. In some of these cases, the adjusting (430) of method 400 comprises adjusting the at least one of the current, the voltage, the pulse width, and the pulse frequency applied to the one or more light emitting devices based on the received wavelength and intensity of the light emitted from each portion of the fluorescent grid. In some of these cases in which there are more than one light emitting devices, the method 400 further comprises varying at least one of the current, the voltage, the pulse width, and the pulse frequency applied to each of the light emitting devices based on the received wavelength and intensity of light emitted from each portion of the fluorescent grid corresponding to the light emitting devices. It should be understood that, in these cases, that at least one of the current, the voltage, the pulse width, and the pulse frequency may be adjusted for all light emitting devices based on the portion of the fluorescent grid that indicates an insufficiency or oversupply in the light energy dose; or, alternatively, that at least one of the current, the voltage, the pulse width, and pulse frequency may be adjusted for each light emitting device (e.g., each LED of an LED array) according to the wavelength and intensity of light received from the portion of the fluorescent grid that corresponds to that light emitting device.

Figure 7A:
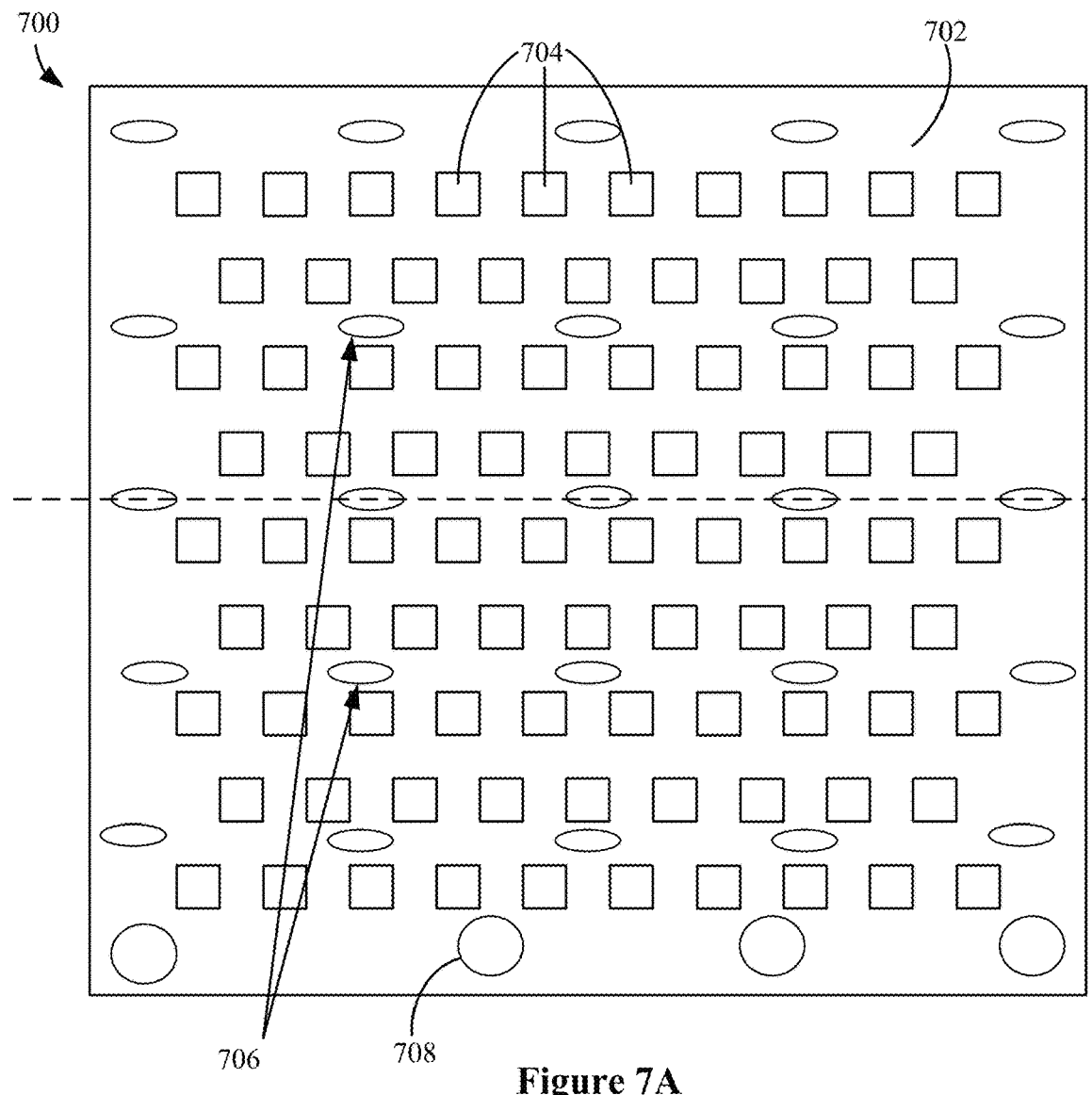
FIG. 7A illustrates a bottom side of an example light disinfection system for delivering light treatment to a potentially compromised surface based on fluorescent feedback.
Figure 7B:
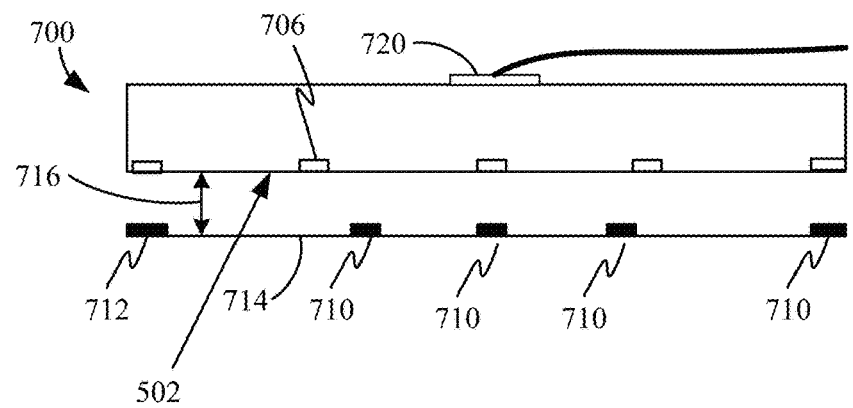
FIG. 7B illustrates a cross-sectional side-view along the dotted line of FIG. 7A

FIG. 7A illustrates a bottom side of an example light disinfection system for delivering light treatment to a potentially compromised surface based on fluorescent feedback. FIG. 7B illustrates a cross-sectional side-view along the dotted line of FIG. 7A. Referring to FIGS. 7A and 7B, the bottom, or front side, 702 of a light emitting substrate 700 of a light disinfection system may be positioned to face the potentially compromised surface 714. Circuitry 720 can be on or in a top, or back side, of the substrate 700. The circuitry 720 can include selection circuitry, comparators, and, in some cases, processing circuitry for the controller. The substrate 700 may be a flexible and/or transparent substrate. In some cases, the substrate 700 may be molded to a shape of the surface receiving the dose of light energy.

In this example, the substrate 700 includes a plurality of LEDs 704 in an array. The number of LEDs 704 in the array can depend on the size of the substrate 700 as well as the lighting characteristics of the LEDs 704. In some cases, the number of LEDs 704 depends on the material covering the LEDs, which can function as a diffusion layer (not shown). Fluorescent light sensors 706 can be located between the LEDs 704. In addition, in some cases, a second type of fluorescent light sensor 708 can be included. The second type of fluorescent light sensor 708 can be used in scenarios where two types of fluorescent material are used, for example, one type to determine positioning of the LEDs 704 and another type to use to determine whether appropriate dose is being applied. In the illustrated example the second type of fluorescent light sensor is shown near an edge of the substrate 700, but embodiments are not limited thereto. In some cases, sensors (e.g., one or more sensors 706, one or more sensors 708, and/or other sensors) can be used to determine distance 716 between the potentially compromised surface 714 and the substrate 700.

One or more fluorescent components 710 may be positioned to be able to emit light that can be captured by sensors 706 disposed between the LEDs 704. The fluorescent components 710 may or may not directly align with the sensors on the substrate 700. One or more fluorescent components 712 may be positioned to be able to emit light that can be captured by sensors 708 In some cases, the same type of sensor can detect the range of fluorescent wavelengths.

In some cases, the one or more fluorescent components 710 may emit a different wavelength and/or intensity of light than the one or more fluorescent components 712, despite receiving light from the same source of LEDs 704. This allows for the one or more sensors 706 to be set up to receive measurements of wavelength and/or intensity of light that are different from the measurements of wavelength and/or intensity of light that the one or more sensors 708 are set up to receive. The differing types of fluorescent materials can be used to define certain regions, for example, where dose is intended to vary for certain areas (e.g., one area is to receive one dose and a second area is to receive a greater dose).

For example, referring back to FIGS. 6C, 6D, and 6E, the plurality of sutures 604 may be made of a fluorescent thread that emits a different wavelength of light (e.g., about 550 nanometers) than the fluorescent component 608 or 610 (e.g., about 590 nanometers). The arrangement of the fluorescent components 608 or 610 and the fluorescent thread of the plurality of sutures 604 may be considered/treated as a grid. Because of this, sensors (e.g., the one or more sensors 706) located in a position corresponding to the plurality of sutures 604 can receive measurements of wavelength and intensity of light emitted from the fluorescent thread to pass along to a controller to carry out a method of treating a potentially compromised surface with a dose of light energy (the method 400). Other sensors (e.g., the one or more sensors 708) located in a position corresponding to the fluorescent component 608 or 610 can receive measurements of wavelength and intensity of light emitted from the fluorescent component 608 or 610 to pass along to a controller carry out a method of treating a potentially compromised surface with a dose of light energy (the method 400). This allows the controller to carry out some or all of the method of treating a potentially compromised surface with a dose of light energy separately for different LEDs in the light emitting device 612 depending on the wavelength and intensity of light received from their corresponding fluorescent components (e.g., 608 or 610 and the fluorescent thread of the plurality of sutures 604). In other words, the controller can vary at least one of the current, the voltage, the pulse width, and the pulse frequency applied to the different LEDs based on the received wavelength and intensity of the light emitted from each portion of the fluorescent grid.

Returning back to FIGS. 7A and 7B, a controller can be set up to carry out some or all of the method of treating a potentially compromised surface with a dose of light energy separately for different LEDs in the substrate 700. For example, LEDs of the plurality of LEDs 704 that are closer to the one or more sensors 706 may be controlled separately from LEDs of the plurality of LEDs 704 that are closer to the one or more sensors 708. Each of the LEDs of the plurality of LEDs 704 that are closer to the one or more sensors 706 may receive a wavelength and intensity of light from a portion of the fluorescent grid corresponding to fluorescent components 710. Each of the LEDs of the plurality of LEDs 704 that are closer to the one or more sensors 708 may receive a wavelength and intensity of light from a portion of the fluorescent grid corresponding to fluorescent components 712. In some cases, the adjusting (430) steps of the method 400 may be performed by a controller such that the all of the plurality of LEDs 704 emit an adequate amount of light that is needed for the area being disinfected by the dose of light energy corresponding to the portion of the fluorescent grid that emits the (relatively) lowest measured intensity of the dose of light energy. In some cases, the adjusting (430 steps of the method 400 may be performed by a controller such that each LED of the plurality of LEDs 704 emits an adequate amount of light energy that is needed for the area being disinfected by the dose of light energy corresponding to the portion of the fluorescent grid for that LED by varying at least one of the current, the voltage, the pulse width, and the pulse frequency applied to that LED. As mentioned above, other circuitry (not shown) may be embedded in the substrate 700.

Figure 8A:
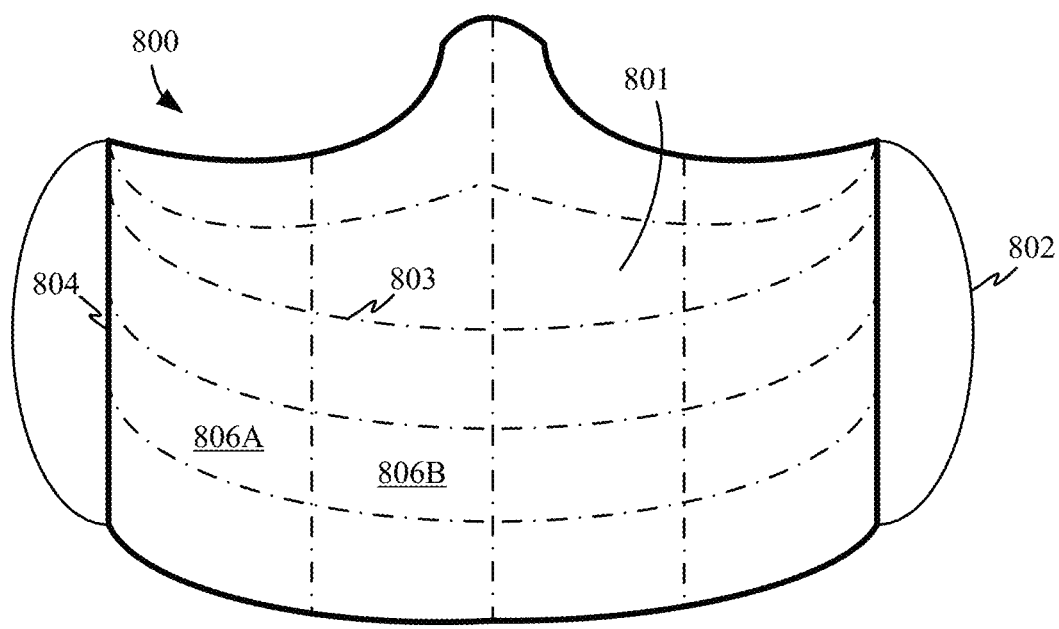
FIG. 8A illustrates a surface of a healthcare mask having a fluorescent component.
Figure 8B:
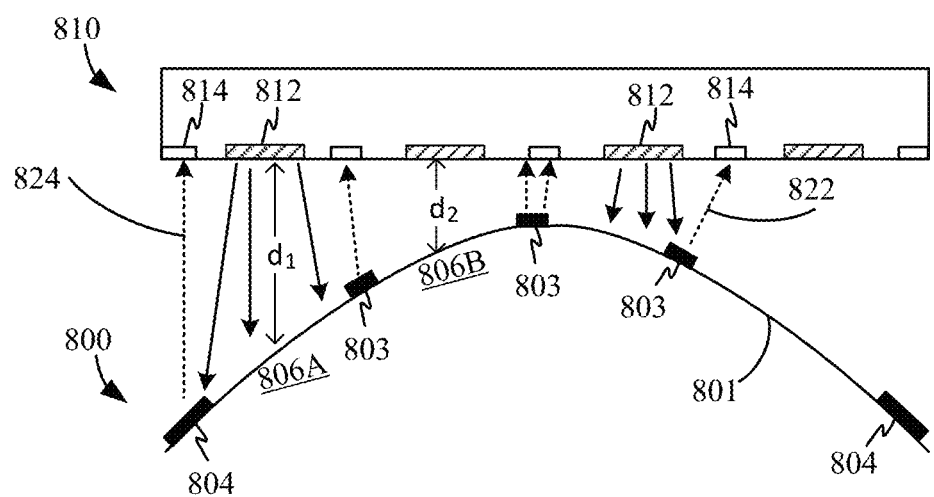
FIG. 8B illustrates a cross-sectional view of a light disinfection system applying a dose of light energy to a surface of a healthcare mask.

FIG. 8A illustrates a surface of a healthcare mask having a fluorescent grid; and FIG. 8B illustrates a cross-sectional view of a light disinfection system applying a dose of light energy to a surface of a healthcare mask. Referring to FIG. 8A, a healthcare mask 800 with a body 801 and bands 802

(e.g., formed of an elastic cord for fitting around a person's ears to secure the body to a person's face) can include a fluorescent component in the form of a fluorescent grid. The fluorescent grid can include internal lines 803 (in a grid pattern) across the body 801 and boundary lines 804 (at the edges of the body 801 of the mask 800). The fluorescent grid defines areas, including a first area 806A and a second area 806B. In some cases, a fluorescent component can be included on or as part of the bands 802.

Referring to FIG. 8B, healthcare mask 800 can be disinfected using a light disinfection system 810 that includes at least one LED 812 and at least one sensor 814 capable of detecting wavelength and intensity of light emitted from the fluorescent components 803, 804 on the body 801 of the healthcare mask 800. In some cases, for example, due to the curvature in the surface 801 of the healthcare facemask 800, the distance d1 between a light emitting portion of the light disinfection system 810 and the first area 806A is different than the distance d2 between the light emitting portion of the light disinfection system 810 and the second area 806B. This difference in distances can affect the dose applied to the region. The sensors 814 can detect that the dose of light energy emitted from an LED 812 is optimal, sub-optimal, or not optimal and make adjustments. For example, the intensity of light 824 emitted from distance around d1 would be less than the intensity of light 822 emitted from a distance around d2 if the LEDs in both areas were operated the same. Here, the LEDs can be operated independently such that the area 806A that has a longer distance can have LEDs applied with power to operate with more intensity than those disinfecting the area 806B.

Although specific examples of grids have been described above, it should be understood that a controller may be configured to receive measurements of wavelengths and intensities of light energy from a portion of a fluorescent grid corresponding to fluorescent component that is arranged in any pattern; and therefore provide a dose of light energy based on that received signal until all portions of the fluorescent grid have received a proper light dose of energy. Furthermore, the described grids may be applied to any surface being disinfected.

In some cases, where a fluorescent grid is used, the controller can map an area to be disinfected, for example, by using the fluorescent grid as markers; generate a heat map of the areas being dosed with light energy based on received fluorescent signals from the different areas; and continuing to operate until all areas have had a proper dose. This method is suitable for areas larger than the area that can receive the light energy dose and/or where the dose may not consistently be applied.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A method of controlling application of light energy for a disinfecting treatment, comprising:
    causing a dose of light energy to be emitted from at least one light emitting device (LED);
    receiving a wavelength and intensity of light emitted from a fluorescent component within an area being disinfected by the dose of light energy, the light emitted from the fluorescent component being due to the dose of light energy impinging the fluorescent component;
    determining whether an appropriate dose of the light energy emitted from the LED impinges the area being disinfected based on the received wavelength and intensity of the light emitted from the fluorescent component due to the dose of light energy impinging the fluorescent component; and
    adjusting at least one of a current, a voltage, a pulse width, and a pulse frequency applied to the at least one LED based on the received wavelength and intensity of the light emitted from the fluorescent component due to the dose of light energy impinging the fluorescent component.

2. The method of claim 1, further comprising:
    determining from the wavelength and intensity of light emitted from the fluorescent component within the area being disinfected that the dose of light energy has been applied for a predetermined length of time; and
    upon determining from the wavelength and intensity of light emitted from the fluorescent component within the area being disinfected that the dose of light energy has been applied for the predetermined length of time, causing the dose of light energy being emitted from the at least one LED to cease.

3. The method of claim 2, further comprising upon determining from the wavelength and intensity of light emitted from the fluorescent component within the area being disinfected that the dose of light energy has been applied for the predetermined length of time, sending a notification that the area being disinfected by the dose of light energy has been successfully disinfected.

4. The method of claim 1, wherein the fluorescent component within the area being disinfected by the dose of light energy is arranged in a fluorescent grid.

5. The method of claim 4, wherein the adjusting at least one of the current, the voltage, the pulse width, and the pulse frequency applied to the at least one LED based on the received wavelength and intensity of the light emitted from the fluorescent component comprises adjusting the at least one of the current, the voltage, the pulse width, and the pulse frequency applied to the at least one LED based on the received wavelength and intensity of the light emitted from each portion of the fluorescent grid.

6. The method of claim 4, wherein the at least one LED is at least two LEDs, the method further comprising varying the at least one of the current, the voltage, the pulse width, and the pulse frequency applied to each of the at least two LEDs based on the received wavelength and intensity of light emitted from portions of the fluorescent grid corresponding to each of the at least two LEDs.

7. The method of claim 1, wherein the fluorescent component within the area being disinfected by the dose of light energy is made of fluorescent thread.

8. A system for controlling application of light energy for a disinfecting treatment, comprising:
    at least one light emitting device (LED) for providing a dose of light energy;
    a fluorescent component within an area being disinfected by the dose of light energy wherein the fluorescent component emits light as a result of the dose of light energy that impinges the fluorescent component;
    at least one sensor capable of sensing a wavelength and corresponding intensity of the light emitted from the fluorescent component within the area being disinfected by the dose of light energy; and a controller coupled to the at least one sensor and the at least one LED to receive a signal from the at least one sensor to determine whether an appropriate dose of light energy emitted from the at least one LED impinges the area being disinfected based on a received wavelength and corresponding intensity of the light emitted from the fluorescent component due to the dose of light energy impinging the fluorescent component and control an output of the at least one LED based on the signal from the at least one sensor.

9. The system of claim 8, wherein the fluorescent component is disposed on or in a transparent bandage.

10. The system of claim 9, wherein the at least one LED is disposed on the transparent bandage and above the fluorescent component.

11. The system of claim 9, wherein the at least one sensor is disposed on the transparent bandage and above the fluorescent component.

12. The system of claim 8, wherein the fluorescent component is arranged in a fluorescent grid.

13. The system of claim 8, wherein the fluorescent component comprises fluorescent thread.

14. The system of claim 8, wherein the controller is configured to:
cause the dose of light energy to be emitted from the at least one LED;
receive, via the at least one sensor, a wavelength and intensity of light emitted from the fluorescent component within the area being disinfected by the dose of light energy; and
adjust at least one of a current, a voltage, a pulse width, and a pulse frequency applied to the at least one LED based on the received wavelength and intensity of the light emitted from the fluorescent component.

15. The system of claim 14, wherein the controller is further configured to:
determine from the wavelength and intensity of light emitted from the fluorescent component within the area being disinfected that the dose of light energy has been applied for a predetermined length of time; and
upon determining from the wavelength and intensity of light emitted from the fluorescent component within the area being disinfected that the dose of light energy has been applied for the predetermined length of time, cause the dose of light energy being emitted from the at least one LED to cease.

16. The system of claim 15, wherein the controller is further configured to:
upon determining from the wavelength and intensity of light emitted from the fluorescent component within the area being disinfected that the dose of light energy has been applied for the predetermined length of time, send a notification that the area being disinfected by the dose of light energy has been successfully disinfected.

17. The system of claim 8, comprising at least two LEDs, wherein each of the at least two LEDs are independently controllable.

18. A storage medium having instructions stored thereon that, when executed, direct a controller to at least:
cause a dose of light energy to be emitted from at least one light emitting device (LED);
receive a wavelength and intensity of light emitted from a fluorescent component within an area being disinfected by the dose of light energy, the light emitted from the fluorescent component being due to the dose of light energy impinging the fluorescent component
determine whether an appropriate dose of the light energy emitted from the LED impinges the area being disinfected based on the received wavelength and intensity of the light emitted from the fluorescent component due to the dose of light energy impinging the fluorescent component; and
adjust at least one of a current, a voltage, a pulse width, and a pulse frequency applied to the at least one LED based on the received wavelength and intensity of the light emitted from the fluorescent component due to the dose of light energy impinging the fluorescent component.

19. The storage medium of claim 18, further comprising instructions that, when executed, direct the controller to:
determine from the wavelength and intensity of light emitted from the fluorescent component within the area being disinfected that the dose of light has been applied for a predetermined length of time; and
upon determining from the wavelength and intensity of light emitted from the fluorescent component within the area being disinfected that the dose of light energy has been applied for the predetermined length of time, cause the dose of light energy being emitted from the at least one LED to cease.

20. The storage medium of claim 19, further comprising instructions that, when executed, direct the controller to:
upon determining from the wavelength and intensity of light emitted from the fluorescent component within the area being disinfected that the dose of light energy has been applied for the predetermined length of time, send a notification that the area being disinfected by the dose of light energy has been successfully disinfected.

* * * * *